United States Patent [19]

Ashby

[11] 3,974,198
[45] Aug. 10, 1976

[54] PROCESS FOR PRODUCING METHYLTRIACETOXYSILANE
[75] Inventor: Bruce A. Ashby, Schenectady, N.Y.
[73] Assignee: General Electric Company, Waterford, N.Y.
[22] Filed: Sept. 2, 1975
[21] Appl. No.: 609,181

[52] U.S. Cl. .......................... 260/448.2 E; 260/413
[51] Int. Cl.² .......................... C07F 7/08; C07F 7/18
[58] Field of Search ...................... 260/448.2 E, 413

[56] References Cited
UNITED STATES PATENTS
3,819,674   6/1974   Rudolph et al. ............... 260/448.2 E

OTHER PUBLICATIONS

Noll, "Chemistry and Technology of Silicones," Academic Press, N.Y. (1968), pp. 108–111.

Primary Examiner—Paul F. Shaver
Attorney, Agent, or Firm—John L. Young; E. Philip Koltos; Frank L. Neuhauser

[57] ABSTRACT

An improved process for producing an acyloxysilane comprising reacting a chlorosilane with a carboxylic acid or a carboxylic acid anhydride in the presence of an iron complexing agent.

8 Claims, No Drawings

PROCESS FOR PRODUCING METHYLTRIACETOXYSILANE

BACKGROUND OF THE INVENTION

The present invention relates to a process for producing acyloxysilane and more particularly the present invention relates to the production of an acyloxysilane with improved yields which are produced by carrying out the reaction in the presence of an iron complexing agent.

Acyloxysilanes are well known cross-linking agents for one-part room temperature vulcanizable silicone rubber compositions. See, for instance, Shaw, U.S. Pat. No. 3,701,755, which issued Oct. 31, 1972. A common type of such an acyloxysilane cross-linking agent is methyltriacetoxysilane. A preferred method for producing such an acyloxysilane cross-linking agent is the reaction of the appropriate chlorosilane with a carboxylic anhydride. The advantage of this reaction with the carboxylic acid anhydride reactant is that it does not produce corrosive by-products and specifically acid by-products which necessitates special handling procedures. However, because of shortages and costs it is not always possible to obtain a carboxylic anhydride for such a process of producing acyloxysilanes. Accordingly, in some cases it is necessary to use a carboxylic acid such as, acetic acid and specifically glacial acetic acid and react it with a chlorosilane to obtain the acyloxy cross-linking agent.

One undesirable aspect of such a process with the carboxylic acid is that hydrochloric acid results as a by-product which acid is highly corrosive.

Another disadvantage of both processes and more specifically the process where the carboxylic acid is utilized as a reactant is that it has been found that yields of desired acyloxysilane are dramatically below what would be anticipated from theoretical calculations. The reason for this low yield and especially in the case where carboxylic acid reactant was utilized was not known prior to this time.

It has now unexpectedly been found that the presence of even traces amount of iron in the reaction media depending on the amount of iron that is present will decrease the yield of the desired acyloxysilane by as much as 20 to 50% or more.

Accordingly, it is one object of the present invention to provide an improved process for producing an acyloxysilane so as to obtain increased yields of the desired product.

It is an additional object of the present invention to provide for a process for improving the yields in producing acyloxysilanes by utilizing in the reaction medium an iron complexing agent.

It is still an additional object of the present invention to provide a simple and efficient method for complexing iron in a process for producing acyloxysilanes so as to result in improved yields of the desired acyloxysilanes.

These and other objects of the present invention are accomplished by means of the disclosure set forth hereinbelow.

SUMMARY OF THE INVENTION

In accordance with the above objects, there is provided by the present invention an improved process for producing acyloxysilanes comprising reacting a compound of the formula, $$R_nSiCl_{4-n} \tag{1}$$

with a compound selected from the class consisting of compounds of the formula, $$R'COOH \tag{2}$$

and compounds of the formula, $$(R'CO)_2O \tag{3}$$

in the presence of an iron complexing agent where R and R' are alkyl radicals of 1 to 8 carbon atoms and a varies from 1 to 3.

The above process is preferably carried out at a concentration of 0.1 to 5% based on the weight of the reactants of the iron complexing agent. Any well known iron complexing agent may be utilized. However, the preferred ones are ethylenediaminetetraacetic acid, phenanthroline, hydroxyquinoline, dipyridyl, acetylacetone, salicylaldehyde and alpha-alanine. The reaction is completed anywhere from 0.5 minutes to 10 hours. Within this time span and if the reaction is carried out in the presence of a solvent, the solvent may be stripped off and any excess acid and chlorides are also stripped off to yield the desired siloxy silane product, and most preferably methyltriacetoxysilane within the range of products covered by the above disclosure.

DESCRIPTION OF THE PREFERRED EMBODIMENT

In the above formulas, R may be an alkyl radical of 1 to 8 carbon atoms but is most preferably methyl and R' may be any alkyl radical of 1 to 8 carbon atoms and is most preferably methyl, a may vary from 1 to 3, is more preferably 1 to 2, and is most preferred to be 1.

It must be appreciated that if the foregoing reaction is carried out in the complete absence of iron that the highest yields are obtained of desired reaction product and the iron complexing agent is not needed. In the case where the carboxylic acid anhydride is utilized in the reaction, the by-products are not very corrosive but, nevertheless, some iron does get into the reaction medium. This is true even where the reactions are carried out in glass lined reactors. As the result of the normal corrosive effects of the by-products, some iron does get into the system and reduces the desired yield by perhaps as much as 10%.

In the case where one of the reactants is a carboxylic acid, the effect is more pronounced since there is given off hydrogen chloride as a by-product which attacks any metal fittings that are exposed to the reaction media which results in the introduction of substantial amounts of iron into the reaction media and thus reducing the desired yield by as much as 20 or more percent. As much as 5 parts per million of the iron in the reaction media will affect the yield. As much as 20 parts per million of iron in the reaction media may reduce the yield by as much as 50% or more.

Accordingly, in accordance with the present invention, it has been found that the yields can be dramatically improved in such processes by carrying out the process in the presence of an iron complexing agent. As set forth above, the iron complexing agent is generally utilized at a concentration of 0.1 to 5% by weight and is preferably utilized at a concentration of 1 to 2% by weight of the chlorosilane and carboxylic acid reactants.

Any well known iron complexing agent may be utilized such as those to be found in the text book Organic Sequestering Agents, S. Chaberek, A. Martell, John Wiley & Sons, Inc., New York, 1959, whose disclosure is hereby incorporated by reference. The more preferred iron complexing agents because of their availability and cheapness are the ones listed above such as, ethylenediaminetetraacetic acid and its alkali metal salts sold by the Dow Chemical Company, Midland, Michigan; 0-phenanthroline sold by Eastman Organic Chemicals, 343 State Street, Rochester, New York; 8-hydroxyquinoline sold by Ashland Chemicals, Fine Chemicals Department, P.O. Box 2219, Columbus, Ohio; 2,2'-dipyridyl sold by Aceto Chemical Co., Inc., 126-02 Northern Boulevard, Flushing, New York; acetylacetone sold by Union Carbide Chemicals and Plastics Division, 270 Park Avenue, New York; salicylaldehyde sold by the Dow Chemical Co., Midland, Michigan and alpha-alanine sold by Degussa, Inc., 2 Penn Plaza, New York.

It should be noted that the above iron complexing agents while they are the most preferred are in a sense exemplary. Any iron complexing agent may be utilized in the present process with various degrees of success. The ones indicated above have been found to be most effective and more specifically, ethylenediaminetetraacetic acid.

It should also be specified that with respect to the concentrations of the above iron complexing agents, the broad range is a general range which has been found to be most suitable. Thus, if less than 0.1% of complexing agent is utilized, then it is usually not found to be very effective and if more than 5% by weight of complexing agent is utilized, it is not found that it fulfills any needed function.

The reaction may be carried out at any temperature of from 25° to 150°C but it is more preferably carried out at room temperature such as 25°C so as to eliminate and minimize the corrosive effect of any acids or corrosive by-products that may be given off. The iron complexing agents specified above will work within the above temperature range. However, high temperature reactions will increase the effectiveness of the acid by-products in attacking metal fittings and adding undesirable amount of iron to the reaction media.

Preferably, the above reaction is carried out in a solvent which may be any inert hydrocarbon solvent but is preferably selected from the class consisting of mineral spirits, toluene, xylene, benzene, hexane, heptane, octane and cyclohexanes. The above solvents are exemplary and are utilized in excess. It is understood that any type of inert hydrocarbon solvent may be utilized.

One of the reactants are dissolved in the solvent with the iron complexing agent in it, the other reactant is added and the material is allowed to react for a period of anywhere from ½ hour to 10 hours. During such reaction period and during this time, after a period of time of say anywhere from ½ to 2 hours, the solvent can be stripped off at elevated temperatures of 50° to 150°C and then any excess chlorides or acids, as well as any other volatile impurities can be removed by stripping them off at such elevated temperatures to result in a high yield of the acyloxysilanes.

Utilizing this process and the iron complexing agent and especially in the case where there is utilized as a reactant the carboxylic acid, there may be obtained yields of the desired acyloxysilanes as high as 80% theoretical or more.

The following examples are given for the purpose of illustrating the invention and are not given for the purpose of limiting the definition of the invention as set forth in the instant specification. All parts are by weight.

EXAMPLE 1

This example was carried out in an all-glass iron-free system in the laboratory. To a solution of 224.3 parts (1.5 mole) of methyltrichlorosilane and 100 milliliters of hexane there was added 315 parts of glacial acetic acid. The addition was carried out over a 2½ hour period at the top of a distilling column by addition to the refluxing mixture of methyltrichlorosilane and hexane. After the addition, the refluxing was continued for 3½ hours. Then the hexane was removed by atmospheric pressure distillation to a pot temperature of 120°C. Next, the system pressure was reduced to 60 Torr and the mixture was refluxed for another hour. This last hour of refluxing was required to reduce the chloride level to less than 100 ppm. Finally, the excess acetic acid was removed by distillation at 60 Torr. The residue remaining which comprised 313 parts had the following analysis by gas chromatography:

| COMPONENT | WT. % |
| --- | --- |
| Dimethyldiacetoxysilane | 0.44 |
| Methyltriacetoxysilane | 93.7 |
| Dimethyltetraacetoxydisiloxane | 5.3 |
| High Boilers | 0.6 |

EXAMPLE 2

The following example was carried out in an all-glass system but with added iron to illustrate the detrimental effect of iron the desired yield of methyltriacetoxysilane. To a solution of 224.3 parts (1.5 mole) of methyltrichlorosilane and 100 milliliters of hexane there was added 315 parts of glacial acetic acid. The addition was carried out over a 2½ hour period which material was added at the top of the distilling column to the refluxing mixture of methyltrichlorosilane and benzene. There was also added at this time 0.027 parts of ferric chloride. After the addition, refluxing was continued for 3½ hours. Then the hexane was removed by atmospheric pressure distillation to a pot temperature of 120°C. Next, the system pressure was reduced to 60 Torr and the mixture was refluxed for another hour. This last hour of refluxing was required to reduce the chloride level to less than 100 ppm. Finally, the excess acetic acid was removed by distillation at 60 Torr. The residue remaining (226 parts) had the following analysis as determined by gas chromatography:

| COMPONENT | WT. % |
| --- | --- |
| Low Boilers | 0.5 |
| Dimethyldiacetoxysilane | 0.3 |
| Methyltriacetoxysilane | 18.7 |
| Dimethyltetraacetoxydisiloxane | 36.3 |
| Tetraacetoxytricyclicsiloxane | 22.8 |
| High Boilers | 21.4 |

EXAMPLE 3

The following example illustrates the effect of an iron complexing agent in carrying out the reaction of Example 1 in an all-glass iron-free system to which iron has been added as set forth in Example 2. To a solution of 224.3 parts (1.5 mole) of methyltrichlorosilane and 100 milliliters of hexane there was added 315 parts of glacial acetic acid. The addition was carried out over a 2½ hour period at the top of a distilling column to the refluxing mixture of methyltrichlorosilane and benzene. To this mixture there was also added at this time 0.027 parts of ferric chloride and 1 part of ethylenediaminetetraacetic acid. After addition, the refluxing was continued for 3½ hours. Then the hexane was removed by atmospheric pressure distillation to a pot temperature of 120°C. Next, the system pressure was reduced to 60 Torr and the mixture was refluxed for another hour. This last hour of refluxing was required to reduce the chloride level to less than 100 ppm. Finally, the excess acetic acid was removed by distillation at 60 Torr. The residue remaining which was 274 parts had the following analysis as determined by gas chromatography:

| COMPONENT | WT. % |
|---|---|
| Dimethyldiacetoxysilane | 0.23 |
| Methyltriacetoxysilane | 78.3 |
| Dimethyltetraacetoxydisiloxane | 18.4 |
| Tetraacetoxytricyclicsiloxane | 1.8 |
| High Boilers | 1.3 |

EXAMPLE 4

This example illustrates an actual plant run utilizing the reactants set forth in Example 1, without the purposeful addition of any iron to the was used was media in any way or manner. The equipment that was an all-glass lined steel equipment.

To a solution of 160 parts of methyltrichlorosilane and 200 parts of hexane, there was added 225 parts of glacial acetic acid. The addition was made over a 2½ hour period at the top of the distilling column to the refluxing mixture of methyltrichlorosilane and hexane. After the addition, refluxing was continued for 3½ hours. Then the hexane was removed by atmospheric pressure distillation to a pot temperature of 120°C. Next, the system pressure was reduced to 60 Torr and the mixture was refluxed for another hour. This last hour of refluxing was required to reduce the chloride level to less than 100 ppm. Finally, the excess acetic acid was removed by distillation at 60 Torr. The residue remaining, 170 parts, had the following analysis by gas chromatography:

| COMPONENT | WT. % |
|---|---|
| Acetic Acid | 4.25 |
| Dimethyldiacetoxysilane | 0.34 |
| Methyltriacetoxysilane | 64.2 |
| Dimethyltetraacetoxydisiloxane | 24.2 |
| High Boilers | 7.1 |

Iron analysis indicated by a typical colormetric analytic method indicated there were 4 parts per million of iron in the final residue.

EXAMPLE 5

The process was run with the same ingredients and same quantities of ingredients as set forth in Example 4, but when the glacial acetic acid was added to the methyltrichlorosilane and hexane there was added 1 part of ethylenediaminetetraacetic acid to the same reaction kettle used in Example 4.

There were 183 parts of residue which when analyzed by gas chromatography was found to have the following analysis:

| COMPONENT | WT. % |
|---|---|
| Low Boilers | 2.6 |
| Dimethyldiacetoxysilane | .4 |
| Methyltriacetoxysilane | 91.9 |
| Dimethyltetraacetoxydisiloxane | 4.6 |
| Pentaacetoxytrimethyltrisiloxane | 0.1 |
| High Boilers | .7 |

As seen with the comparison of results of Examples 1 and 2, the presence of iron in the reaction system can decrease the yield of the desired methyltriacetoxysilane by as much as 60% or more.

It should also be noted with respect to the experiments set forth in Examples 4 and 5, that the presence of iron contaminates in the reaction media and even traces amount of iron such as, 4 parts per million can lower the yields by measurable amounts and that the addition of an iron complexing agent can increase the yields of the present process by 20% by weight or more depending on how much iron gets accidentally introduced into the reaction medium. As can be imagined, this will vary from batch to batch depending on the normal variancies and reaction conditions from reaction to reaction. It is important to note that the presence of the iron complexing agent in accordance with the present invention can standardize the yield of product that is obtained from batch to batch and prevent the variances that were present in the past.

It is important impotant to note that after the reaction is terminated and in accordance with the above description of the present process given herein before, various reaction temperatures, pressures and methods can be used to remove the reaction solvent, any excess acid and any chlorides that might be present in the reaction media. Depending on the use to which the material is finally put to, it is only necessary to control the amount of any excess acid or any chlorides that might be present in the final product. For most purposes, the reaction media should be stripped of all excess acid since any acid that is in the product is below 10 parts per million and such that the chloride content in the final residue is below 100 parts per million. If the acyloxysilanes are to be used as cross-linking agents for room temperature vulcanizable silicone rubber compositions, the materials in the residue as identified in the above examples may then be separated and purified by well known distillation techniques.

I claim:

1. An improved process for producing an acyloxysilane comprising reacting a compound of the formula, $$R_aSiCl_{4-a}$$

with a compound selected from the class consisting of compounds of the formula, $$R'COOH$$

and compounds of the formula, (R'CO)₂O in the presence of an iron complexing agent where R and R' are alkyl radicals of 1 to 8 carbon atoms and a varies from 1 to 3.

2. The process of claim 1 wherein R and R' are methyl and a is 1.

3. The process of claim 1 wherein the reaction is carried out at a temperature varying from 25° to 150°C.

4. The process of claim 1 wherein the iron complexing agent is present at a concentration of 0.1 to 5% based on the weight of the reactants.

5. The process of claim 1 wherein the complexing agent is selected from the class consisting of ethylenediaminetetraacetic acid, phenanthroline, hydroxyquinoline, dipyridyl, acetylacetone, salicylaldehyde and alpha-alanine.

6. The process of claim 1 wherein said process is carried out in a solvent selected from the class consisting of mineral spirits, toluene, xylene, benzene, hexane, heptane, octane and cyclohexane.

7. The process of claim 6 wherein said reaction is carried out in 0.5 to 10 hours.

8. The process of claim 7 further comprising stripping off said solvent at the end of the reaction period and removing excess acids and chlorides.

* * * * *